United States Patent
Housman

(10) Patent No.: US 9,788,828 B2
(45) Date of Patent: *Oct. 17, 2017

(54) MINIATURIZED DUAL DRIVE OPEN ARCHITECTURE SUTURE ANCHOR

(71) Applicant: SMITH & NEPHEW, INC., Memphis, TN (US)

(72) Inventor: Mark Edwin Housman, North Attelborough, MA (US)

(73) Assignee: Smith & Nephew, Inc., Memphis, TN (US)

(*) Notice: Subject to any disclaimer, the term of this patent is extended or adjusted under 35 U.S.C. 154(b) by 97 days.

This patent is subject to a terminal disclaimer.

(21) Appl. No.: 14/869,165

(22) Filed: Sep. 29, 2015

(65) Prior Publication Data

US 2016/0120534 A1 May 5, 2016

Related U.S. Application Data

(63) Continuation of application No. 13/838,942, filed on Mar. 15, 2013, now Pat. No. 9,155,531.

(51) Int. Cl.
*A61B 17/04* (2006.01)
*A61B 17/88* (2006.01)
(Continued)

(52) U.S. Cl.
CPC ........ *A61B 17/0401* (2013.01); *A61B 17/869* (2013.01); *A61B 17/8877* (2013.01);
(Continued)

(58) Field of Classification Search
CPC .............. A61B 17/0401; A61B 17/869; A61B 17/8877; A61B 17/888; A61B 2017/0409;
(Continued)

(56) References Cited

U.S. PATENT DOCUMENTS 2,288,864 A  7/1942  Whitehead et al.
3,316,795 A  5/1967  Tann
(Continued)

FOREIGN PATENT DOCUMENTS

CN  2732211  10/2005
CN  1701772 A  11/2005
(Continued)

OTHER PUBLICATIONS

Office Action from related Russian Application No. 2015147534/20(073143) issued Jun. 29, 2016.
(Continued)

*Primary Examiner* — Ryan J Severson
(74) *Attorney, Agent, or Firm* — Burns & Levinson LLP; Joseph M. Maraia

(57) ABSTRACT

The disclosure provides examples of an open architecture anchor for securing soft tissue to bone, for example, to repair a torn rotor cuff. The anchor includes at least one open helical coil defining a polygonal internal volume and at least one rib disposed within the polygonal internal volume and connected to at least two turns of the at least one open helical coil. The at least one rib is sized to engage a driver and a combination of the at least one rib and the polygonal internal volume is sized to provide an anchor drive torque required to drive the anchor into bone.

6 Claims, 7 Drawing Sheets

(51) Int. Cl.
*A61B 17/86* (2006.01)
*A61F 2/08* (2006.01)

(52) U.S. Cl.
CPC ..... *A61B 17/888* (2013.01); *A61B 2017/0409* (2013.01); *A61B 2017/0441* (2013.01); *A61B 2017/0445* (2013.01); *A61B 2017/0448* (2013.01); *A61B 2017/0458* (2013.01); *A61F 2/0811* (2013.01); *A61F 2002/0841* (2013.01); *A61F 2002/0852* (2013.01); *A61F 2230/0021* (2013.01)

(58) Field of Classification Search
CPC .... A61B 2017/0411; A61B 2017/0414; A61B 2017/044; A61B 2017/0441; A61B 2017/0445; A61B 2017/0446; A61B 2017/0448; A61B 2017/0458; A61F 2/0811; A61F 2002/0817; A61F 2002/0841
See application file for complete search history.

(56) References Cited

U.S. PATENT DOCUMENTS

| | | | |
|---|---|---|---|
| 3,320,783 | A | 5/1967 | Kerr |
| 3,499,222 | A | 3/1970 | Linkow et al. |
| 3,716,058 | A | 2/1973 | Tanner |
| 3,821,975 | A | 7/1974 | Haker |
| 3,869,942 | A | 3/1975 | DeCaro |
| 3,874,258 | A | 4/1975 | Semola et al. |
| 4,027,572 | A | 6/1977 | Burge |
| 4,177,797 | A | 12/1979 | Baylis et al. |
| D288,777 | S | 3/1987 | Kwon |
| 4,653,489 | A | 3/1987 | Tronzo |
| 4,738,255 | A | 4/1988 | Goble et al. |
| 4,741,651 | A | 5/1988 | Despres |
| 4,834,757 | A | 5/1989 | Brantigan |
| 4,854,311 | A | 8/1989 | Steffee |
| RE33,114 | E | 11/1989 | Chiavon |
| 4,913,143 | A | 4/1990 | Oloff et al. |
| 4,961,740 | A * | 10/1990 | Ray ............ A61B 17/1637 606/247 |
| 4,988,351 | A | 1/1991 | Paulos et al. |
| 5,026,373 | A * | 6/1991 | Ray ............ A61B 17/1637 606/279 |
| 5,055,104 | A * | 10/1991 | Ray ............ A61B 17/1757 606/247 |
| 5,094,133 | A | 3/1992 | Schreiber |
| 5,116,337 | A | 5/1992 | Johnson |
| 5,129,904 | A | 7/1992 | Illi |
| 5,129,906 | A | 7/1992 | Ross et al. |
| 5,139,520 | A | 8/1992 | Rosenberg |
| 5,197,967 | A | 3/1993 | Wilson |
| 5,236,431 | A | 8/1993 | Gogolewski et al. |
| 5,242,447 | A | 9/1993 | Borzone |
| 5,312,214 | A | 5/1994 | Morton |
| 5,354,299 | A | 10/1994 | Coleman |
| 5,364,400 | A | 11/1994 | Rego, Jr. et al. |
| 5,370,662 | A | 12/1994 | Stone et al. |
| 5,383,878 | A | 1/1995 | Roger et al. |
| 5,407,427 | A | 4/1995 | Zhu et al. |
| 5,411,506 | A | 5/1995 | Goble et al. |
| 5,411,523 | A | 5/1995 | Goble |
| 5,423,823 | A | 6/1995 | Schmieding |
| 5,431,660 | A | 7/1995 | Burke |
| 5,447,533 | A | 9/1995 | Vachon et al. |
| 5,464,427 | A | 11/1995 | Curtis et al. |
| 5,470,334 | A | 11/1995 | Ross et al. |
| 5,531,780 | A | 7/1996 | Vachon |
| 5,571,139 | A | 11/1996 | Jenkins, Jr. |
| 5,573,548 | A | 11/1996 | Nazre et al. |
| 5,593,409 | A | 1/1997 | Michelson |
| 5,609,635 | A | 3/1997 | Michelson |
| 5,609,636 | A | 3/1997 | Kohrs et al. |
| 5,626,613 | A | 5/1997 | Schmieding |
| 5,632,747 | A | 5/1997 | Scarborough |
| 5,645,547 | A | 7/1997 | Coleman |
| 5,658,285 | A | 8/1997 | Marnay et al. |
| 5,676,545 | A | 10/1997 | Jones |
| 5,681,352 | A | 10/1997 | Clancy, III et al. |
| 5,688,285 | A | 11/1997 | Yamada |
| 5,690,676 | A | 11/1997 | Dipoto et al. |
| 5,695,497 | A * | 12/1997 | Stahelin ............ F16B 23/0007 606/104 |
| 5,702,397 | A | 12/1997 | Goble et al. |
| 5,709,683 | A | 1/1998 | Bagby |
| 5,802,794 | A | 9/1998 | Robson |
| 5,833,715 | A | 11/1998 | Vachon et al. |
| 5,876,405 | A | 3/1999 | Del Rio |
| 5,888,227 | A | 3/1999 | Cottle |
| 5,891,146 | A | 4/1999 | Simon et al. |
| 5,921,982 | A | 7/1999 | Lesh et al. |
| 5,951,560 | A | 9/1999 | Simon et al. |
| 5,961,524 | A | 10/1999 | Crombie |
| 5,964,783 | A | 10/1999 | Grafton et al. |
| 5,968,047 | A | 10/1999 | Reed |
| 5,968,098 | A * | 10/1999 | Winslow ............ A61B 17/025 606/248 |
| 5,984,967 | A | 11/1999 | Zdeblick et al. |
| 6,008,433 | A | 12/1999 | Stone |
| 6,039,762 | A | 3/2000 | McKay |
| 6,086,593 | A | 7/2000 | Bonutti |
| 6,096,060 | A | 8/2000 | Fitts et al. |
| 6,097,986 | A | 8/2000 | Janke et al. |
| 6,132,435 | A | 10/2000 | Young |
| 6,146,073 | A | 11/2000 | Kobusch |
| 6,196,780 | B1 | 3/2001 | Wakai et al. |
| 6,214,031 | B1 | 4/2001 | Schmieding et al. |
| 6,235,057 | B1 | 5/2001 | Roger et al. |
| 6,283,973 | B1 | 9/2001 | Hubbard et al. |
| 6,302,632 | B1 | 10/2001 | Lin |
| 6,360,129 | B1 | 3/2002 | Ley et al. |
| 6,443,989 | B1 | 9/2002 | Jackson |
| 6,447,545 | B1 | 9/2002 | Bagby |
| 6,488,683 | B2 | 12/2002 | Lieberman |
| 6,503,251 | B1 * | 1/2003 | Shadduck .......... A61B 17/0401 606/232 |
| 6,511,499 | B2 | 1/2003 | Schmieding et al. |
| 6,514,257 | B2 | 2/2003 | Dovesi et al. |
| 6,517,542 | B1 | 2/2003 | Papay et al. |
| 6,527,774 | B2 * | 3/2003 | Lieberman ............ A61B 17/70 606/301 |
| 6,544,265 | B2 | 4/2003 | Lieberman |
| 6,551,319 | B2 | 4/2003 | Lieberman |
| 6,551,320 | B2 | 4/2003 | Lieberman |
| 6,551,322 | B1 | 4/2003 | Lieberman |
| 6,554,830 | B1 | 4/2003 | Chappius |
| 6,569,188 | B2 | 5/2003 | Grafton et al. |
| 6,589,245 | B1 | 7/2003 | Weiler et al. |
| 6,604,945 | B1 | 8/2003 | Jones |
| 6,620,195 | B2 | 9/2003 | Goble et al. |
| 6,626,917 | B1 | 9/2003 | Craig |
| 6,648,903 | B1 | 11/2003 | Pierson |
| 6,656,183 | B2 | 12/2003 | Colleran et al. |
| 6,666,888 | B1 | 12/2003 | Jackson |
| 6,685,728 | B2 * | 2/2004 | Sinnott ............ A61B 17/0401 606/232 |
| 6,818,010 | B2 | 11/2004 | Eichhorn et al. |
| 6,823,871 | B2 | 11/2004 | Schmieding |
| 6,855,168 | B2 | 2/2005 | Crozet |
| 6,857,343 | B1 | 2/2005 | Easterbrooks et al. |
| 6,863,671 | B1 | 3/2005 | Strobel et al. |
| 6,875,216 | B2 | 4/2005 | Wolf |
| 6,887,194 | B2 | 5/2005 | Hart et al. |
| 6,908,465 | B2 | 6/2005 | Von Hoffmann et al. |
| 6,942,669 | B2 | 9/2005 | Kurc |
| 6,942,684 | B2 | 9/2005 | Bonutti |
| 6,953,462 | B2 | 10/2005 | Lieberman |
| 7,018,412 | B2 | 3/2006 | Ferreira et al. |
| 7,033,372 | B1 | 4/2006 | Cahalan |
| 7,070,586 | B2 | 7/2006 | Hart et al. |
| 7,083,647 | B1 | 8/2006 | Sklar et al. |
| 7,090,690 | B2 | 8/2006 | Foerster et al. |

(56) References Cited

U.S. PATENT DOCUMENTS

| | | |
|---|---|---|
| 7,147,641 B2 | 12/2006 | Chen |
| 7,189,251 B2 | 3/2007 | Kay |
| 7,195,634 B2 | 3/2007 | Schmieding et al. |
| 7,217,279 B2 | 5/2007 | Reese |
| 7,226,469 B2 | 6/2007 | Benavitz et al. |
| 7,235,079 B2 | 6/2007 | Jensen et al. |
| 7,322,978 B2 | 1/2008 | West |
| 7,322,986 B2 | 1/2008 | Wolf |
| 7,335,221 B2 | 2/2008 | Collier et al. |
| 7,371,244 B2 | 5/2008 | Chatlynne et al. |
| 7,442,202 B2 | 10/2008 | Dreyfuss |
| 7,510,558 B2 | 3/2009 | Tallarida et al. |
| 7,572,264 B2 | 8/2009 | Null et al. |
| 7,575,572 B2 | 8/2009 | Sweeney |
| 7,585,311 B2 | 9/2009 | Green et al. |
| 7,594,929 B2 | 9/2009 | Collette |
| 7,601,165 B2 | 10/2009 | Stone |
| 7,601,167 B2 | 10/2009 | Lieberman |
| 7,608,097 B2 | 10/2009 | Kyle |
| 7,608,098 B1 | 10/2009 | Stone et al. |
| 7,749,250 B2 | 7/2010 | Stone et al. |
| 7,857,830 B2 | 12/2010 | Stone et al. |
| 7,867,252 B2 | 1/2011 | Criscuolo et al. |
| 7,883,529 B2 * | 2/2011 | Sinnott ............... A61B 17/0401 |
| | | 606/232 |
| 7,896,902 B2 | 3/2011 | Jeon et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 * | 3/2011 | Stone ............... A61B 17/0642 |
| | | 606/104 |
| 7,935,138 B1 | 5/2011 | Richelsoph |
| 7,942,862 B2 | 5/2011 | Hart et al. |
| 7,993,369 B2 | 8/2011 | Dreyfuss et al. |
| 8,034,090 B2 * | 10/2011 | Stone ............... A61B 17/0642 |
| | | 606/300 |
| 8,118,312 B2 | 2/2012 | Walters |
| 8,167,906 B2 * | 5/2012 | Cauldwell .......... A61B 17/0401 |
| | | 606/232 |
| 8,251,998 B2 | 8/2012 | Hoeppner et al. |
| 8,252,006 B2 | 8/2012 | Ortiz et al. |
| 8,343,186 B2 | 1/2013 | Dreyfuss et al. |
| 8,372,124 B2 | 2/2013 | Paulk et al. |
| 8,430,909 B2 | 4/2013 | Dreyfuss |
| 8,449,613 B2 | 5/2013 | Crozet |
| 8,480,686 B2 | 7/2013 | Bakos et al. |
| 8,496,662 B2 | 7/2013 | Novak et al. |
| 8,506,596 B2 | 8/2013 | Stone et al. |
| 8,597,328 B2 * | 12/2013 | Cauldwell .......... A61B 17/0401 |
| | | 606/232 |
| 8,623,049 B2 | 1/2014 | Ward |
| 8,623,052 B2 | 1/2014 | Dreyfuss et al. |
| 8,636,799 B2 | 1/2014 | Sklar et al. |
| 8,663,672 B2 | 3/2014 | Manrique et al. |
| 8,672,967 B2 | 3/2014 | Dimatteo et al. |
| 8,715,282 B2 | 5/2014 | Pool |
| 8,801,755 B2 | 8/2014 | Dreyfuss et al. |
| 8,814,935 B2 | 8/2014 | Paulos |
| 8,821,541 B2 | 9/2014 | Dreyfuss et al. |
| 8,834,538 B2 | 9/2014 | Donnelly et al. |
| 8,882,801 B2 | 11/2014 | Dimatteo et al. |
| 8,900,279 B2 | 12/2014 | Assell et al. |
| 8,974,505 B2 | 3/2015 | Sawa et al. |
| 8,979,848 B2 | 3/2015 | Butters et al. |
| 8,979,865 B2 * | 3/2015 | Fan ..................... A61F 2/0805 |
| | | 606/104 |
| 9,138,220 B2 | 9/2015 | Hernandez |
| 9,155,531 B2 * | 10/2015 | Housman ........... A61B 17/0401 |
| 9,162,350 B2 | 10/2015 | Nino et al. |
| 9,237,887 B2 | 1/2016 | Wack et al. |
| 9,265,494 B2 | 2/2016 | Hester et al. |
| 9,277,911 B2 | 3/2016 | Hernandez |
| 9,308,080 B2 * | 4/2016 | Housman ........... A61B 17/0401 |
| 9,393,006 B2 * | 7/2016 | Housman ........... A61B 17/0401 |
| 9,408,613 B2 | 8/2016 | Kehres et al. |
| 9,427,270 B2 * | 8/2016 | Housman ........... A61B 17/8625 |
| 9,439,644 B2 | 9/2016 | Lizardi |
| 9,526,488 B2 * | 12/2016 | Arai .................... A61B 17/0401 |
| 9,579,188 B2 * | 2/2017 | Bowman .............. A61F 2/0811 |
| 9,642,611 B2 | 5/2017 | Housman et al. |
| 2002/0052629 A1 | 5/2002 | Morgan et al. |
| 2002/0055742 A1 * | 5/2002 | Lieberman ............ A61B 17/70 |
| | | 606/301 |
| 2002/0099382 A1 | 7/2002 | Salazar et al. |
| 2002/0111653 A1 | 8/2002 | Foerster |
| 2003/0055431 A1 | 3/2003 | Brannon |
| 2003/0065361 A1 | 4/2003 | Dreyfuss |
| 2003/0065374 A1 | 4/2003 | Honeck |
| 2003/0078585 A1 | 4/2003 | Johnson et al. |
| 2003/0125749 A1 | 7/2003 | Yuan et al. |
| 2003/0195529 A1 | 10/2003 | Takamoto et al. |
| 2004/0030343 A1 | 2/2004 | Kurc |
| 2004/0073216 A1 | 4/2004 | Lieberman |
| 2004/0093032 A1 * | 5/2004 | Sinnott ............... A61B 17/0401 |
| | | 606/232 |
| 2004/0122424 A1 | 6/2004 | Ferree |
| 2004/0153074 A1 | 8/2004 | Bojarski et al. |
| 2005/0159727 A1 | 7/2005 | Lesh |
| 2005/0222681 A1 * | 10/2005 | Richley ................... A61F 2/446 |
| | | 623/17.11 |
| 2005/0234458 A1 | 10/2005 | Huebner |
| 2005/0250984 A1 | 11/2005 | Lam et al. |
| 2005/0250985 A1 | 11/2005 | Saadat et al. |
| 2005/0250987 A1 | 11/2005 | Ewers et al. |
| 2005/0250988 A1 | 11/2005 | Ewers et al. |
| 2005/0267478 A1 | 12/2005 | Corradi et al. |
| 2006/0030948 A1 * | 2/2006 | Manrique ............ A61B 17/866 |
| | | 623/23.13 |
| 2006/0079895 A1 | 4/2006 | McLeer |
| 2006/0079903 A1 | 4/2006 | Wong |
| 2006/0089651 A1 | 4/2006 | Trudeau et al. |
| 2006/0100627 A1 * | 5/2006 | Stone ................. A61B 17/0642 |
| | | 424/426 |
| 2006/0149266 A1 | 7/2006 | Cordasco |
| 2006/0247642 A1 | 11/2006 | Stone et al. |
| 2006/0253080 A1 | 11/2006 | Tulleken et al. |
| 2006/0276841 A1 | 12/2006 | Barbieri et al. |
| 2007/0093895 A1 | 4/2007 | Donnelly et al. |
| 2007/0122764 A1 | 5/2007 | Balfour et al. |
| 2007/0142849 A1 | 6/2007 | Ewers et al. |
| 2007/0198019 A1 | 8/2007 | Schomer et al. |
| 2007/0203498 A1 | 8/2007 | Gerber et al. |
| 2008/0154314 A1 | 6/2008 | McDevitt |
| 2008/0275431 A1 | 11/2008 | Stone et al. |
| 2009/0024174 A1 | 1/2009 | Stark |
| 2009/0042951 A1 | 2/2009 | Danziger |
| 2009/0076544 A1 * | 3/2009 | DiMatteo ........... A61B 17/0401 |
| | | 606/232 |
| 2009/0118776 A1 | 5/2009 | Kelsch et al. |
| 2009/0125071 A1 | 5/2009 | Skinlo et al. |
| 2009/0187216 A1 | 7/2009 | Schmieding et al. |
| 2009/0292321 A1 | 11/2009 | Collette |
| 2009/0319043 A1 | 12/2009 | McDevitt et al. |
| 2010/0094297 A1 | 4/2010 | Parmigiani |
| 2010/0094352 A1 | 4/2010 | Iott et al. |
| 2010/0106166 A1 | 4/2010 | Cropper et al. |
| 2010/0274298 A1 | 10/2010 | Schiff |
| 2011/0054526 A1 * | 3/2011 | Stone ................. A61B 17/0401 |
| | | 606/232 |
| 2011/0112576 A1 | 5/2011 | Nguyen et al. |
| 2011/0130760 A1 | 6/2011 | Anderson et al. |
| 2011/0213426 A1 | 9/2011 | Yedlicka et al. |
| 2011/0224727 A1 * | 9/2011 | Housman ........... A61B 17/0401 |
| | | 606/232 |
| 2011/0319933 A1 | 12/2011 | Tepic |
| 2012/0041448 A1 | 2/2012 | Schumacher et al. |
| 2012/0059384 A1 | 3/2012 | Fan et al. |
| 2012/0179163 A1 | 7/2012 | Housman et al. |
| 2012/0330420 A1 | 12/2012 | Brodke et al. |
| 2013/0158596 A1 | 6/2013 | Miller et al. |
| 2013/0158610 A1 | 6/2013 | Hernandez |

(56) References Cited

U.S. PATENT DOCUMENTS

| | | | |
|---|---|---|---|
| 2013/0178901 A1* | 7/2013 | Arai | A61B 17/0401 606/233 |
| 2014/0081339 A1* | 3/2014 | Bowman | A61F 2/0811 606/304 |
| 2014/0142697 A1 | 5/2014 | Sklar et al. | |
| 2014/0148850 A1 | 5/2014 | Dimatteo et al. | |
| 2014/0172016 A1* | 6/2014 | Housman | A61B 17/0401 606/232 |
| 2014/0277129 A1* | 9/2014 | Arai | A61B 17/0401 606/232 |
| 2014/0277130 A1 | 9/2014 | Housman | |
| 2014/0277188 A1 | 9/2014 | Poulos | |
| 2014/0277192 A1* | 9/2014 | Housman | A61B 17/8625 606/309 |
| 2015/0196388 A1* | 7/2015 | Housman | A61B 17/0401 606/304 |
| 2015/0327984 A1* | 11/2015 | Arai | A61B 17/0401 606/232 |
| 2016/0235399 A1* | 8/2016 | Housman | A61B 17/0401 |
| 2016/0374661 A1* | 12/2016 | Housman | A61B 17/0401 606/232 |
| 2017/0014224 A1* | 1/2017 | Arai | A61B 17/0401 |
| 2017/0020589 A1* | 1/2017 | Bowman | A61F 2/0811 |
| 2017/0049438 A1* | 2/2017 | Arai | A61B 17/0401 |

FOREIGN PATENT DOCUMENTS

| | | |
|---|---|---|
| CN | 1829479 | 9/2006 |
| CN | 101002703 | 7/2007 |
| CN | 101031248 | 9/2007 |
| CN | 101422381 A | 5/2009 |
| CN | 101573078 | 11/2009 |
| CN | 201436022 U | 4/2010 |
| CN | 102068305 A | 5/2011 |
| CN | 102475586 | 5/2012 |
| CN | 102512253 A | 6/2012 |
| CN | 102525580 | 7/2012 |
| CN | 102525583 A | 7/2012 |
| CN | 102551821 A | 7/2012 |
| CN | 102781370 | 11/2012 |
| CN | 102905636 A | 1/2013 |
| CN | 102573662 B | 8/2015 |
| EP | 05202698 A1 | 9/1992 |
| EP | 0538895 | 6/1993 |
| EP | 0669110 | 11/1995 |
| EP | 0682917 | 11/1995 |
| EP | 0686373 A1 | 12/1995 |
| EP | 0796593 | 3/1998 |
| EP | 0686373 B1 | 3/2001 |
| EP | 1093774 | 4/2001 |
| EP | 1147751 | 10/2001 |
| EP | 1234637 A2 | 8/2002 |
| EP | 1430843 A2 | 6/2004 |
| EP | 1917926 B1 | 11/2009 |
| EP | 2036501 | 9/2010 |
| EP | 2422712 A1 | 2/2012 |
| EP | 2596758 A1 | 5/2013 |
| EP | 2601894 | 6/2013 |
| EP | 2422711 | 10/2015 |
| FR | 2760355 | 9/1998 |
| FR | 2803739 | 7/2001 |
| FR | 2846867 | 5/2004 |
| FR | 2879915 A1 | 6/2006 |
| GB | 2294399 A | 5/1996 |
| JP | H10-000200 | 1/1998 |
| JP | 2005-529650 | 10/2005 |
| JP | 2005529650 | 10/2005 |
| JP | 2006212449 A | 8/2006 |
| JP | 2006-305348 A | 11/2006 |
| WO | 1996-08205 | 3/1996 |
| WO | 1996-19947 | 7/1996 |
| WO | 1998-02117 | 1/1998 |
| WO | 1998-26717 | 6/1998 |
| WO | 03063713 A1 | 8/2003 |
| WO | 03103507 A2 | 12/2003 |
| WO | 20060055516 | 5/2006 |
| WO | 2007093192 A1 | 8/2007 |
| WO | 2008021474 A2 | 2/2008 |
| WO | 2009-042951 | 4/2009 |
| WO | 2010009217 A1 | 1/2010 |
| WO | 2010/017584 | 2/2010 |
| WO | 2010-017631 | 2/2010 |
| WO | 2010053708 A1 | 5/2010 |
| WO | 2011059995 A2 | 5/2011 |
| WO | 2011060022 A2 | 5/2011 |
| WO | 2011112776 A1 | 9/2011 |
| WO | 20120129388 | 9/2012 |
| WO | 2012-171011 | 12/2012 |

OTHER PUBLICATIONS

Communication from EPO from related European Application No. 12711719.0-1666 issued Jul. 28, 2016.
Office Action from related EPO Application No. 14716107.9-1664 issued Mar. 23, 2017.
Notice of Reasons for Rejection from related Japanese Application No. 2014-514625 issued Jun. 13, 2016.
Substantive Examination Report from related Mexico Patent Application No. MX/a/2013/010383 mailed Jan. 19, 2016.
Notice of Reasons for Rejection for related Japanese Application No. 2013-558094 mailed Feb. 2, 2016.
Third Office Action for related Chinese Patent Application No. 2011-80013194.3 issued Aug. 21, 2015.
Second Office Action for related Chinese Patent Application No. 201280022627.6 issued Sep. 16, 2015.
Substantive Examination for related Mexican Patent Application No. MX/a/2013/010383 issued Aug. 12, 2015.
Patent Examination Report No. 1 for related Australian Patent Application No. 2012229152 Issued Aug. 18, 2015.
Office Action from related Mexican Application No. MX/a/2013/010383 issued May 3, 2016.
Decision of Rejection on related Japanese Patent Application No. 2012-557236 mailed Oct. 9, 2015.
Communication from related European Patent Application No. 09761114.9 mailed Dec. 3, 2015.
Communication from related European Patent Application No. 11710940.5 mailed Dec. 8, 2015.
First Office Action for related Chinese Patent Application No. 201280038677.3 issued Sep. 6, 2015.
Patent Examination Report No. 1 for related Australian Patent Application No. 2012267924 mailed Dec. 22, 2015.
Office Action and Search Report from related Chinese Application No. 201480032876.2 issued Oct. 19, 2016.
Office Action from related Chinese Application No. 201280038677.3 issued Nov. 28, 2016.
Office Action from related Japanese Application No. 2014-514625 issued Dec. 19, 2016.
Office Action from related Japanese Application No. 2013-558094 issued Sep. 5, 2016.
Substantive Examination of related Russian Application No. 2013144961/14(069526) mailed Dec. 23, 2015.
Second Office Action from related Chinese Application No. 201280038677.3 issued May 5, 2016.
International Preliminary Report on Patentability for related International Application No. PCT/US2014/033535, mailed Oct. 22, 2015.
International Preliminary Report on Patentability from related PCT Application No. PCT/US2014/066389 issued May 24, 2016.
Office Action from related Russian Application No. 2016124173/20(037886) issued Jan. 19, 2017.
Office Communication from related European Application No. 14712930.8-1662 issued Nov. 24, 2016.
First Office Action from related Chinese Application No. 201480012203.0 issued Aug. 17, 2016.
Third Office Action from related Chines Application No. 201280022627.6 issued Mar. 4, 2016.
Biomet brochure "Bio-Core TM Interference Screw", 2007.

(56) References Cited

OTHER PUBLICATIONS

Communication from related European Application No. 12711719.0-1666 dated Jul. 28, 2016.
Decision of Rejections for Japanese Patent Application No. 2011-538642, dated Jun. 2, 2014.
First Office Action for Chinese Patent Application No. 201480073698.8 dated May 2, 2017.
First Office Action for Chinese Patent Application No. 200980155954.7, dated Apr. 12, 2013.
First Office Action for Chinese Patent Application No. 201180013194.3, dated Jul. 21, 2014.
First Office Action for Chinese Patent Application No. 201280022627.6, dated Apr. 13, 2015.
Hunt, Patrick, D.V.M. et al. "Development of a Perforated Biodegradable Interference Screw", Arthroscopy: The Journal of Arthroscopic and Related Surgery, vol. 21, No. 3, Mar. 2005; pp. 258-265.
International Search and Written Opinion for PCT/US2009/065304 dated Jun. 5, 2013.
International Search and Written Opinion for PCT/US2011/027837 dated May 19, 2011.
International Search and Written Opinion for PCT/US2012/028803 dated Oct. 24, 2010.
International Search and Written Opinion for PCT/US2012/041298 dated Jun. 5, 2013.
International Search and Written Opinion for PCT/US2014/020747 dated Jun. 6, 2014.
International Search and Written Opinion for PCT/US2014/022539 dated Jun. 27, 2014.
International Search and Written Opinion for PCT/US2014/033535 dated Jul. 18, 2014.
International Search and Written Opinion for PCT/US2014/066389 dated Feb. 17, 2015.
Notice of Reasons for Rejection for Japanese Patent Application No. 2012-557236 dated Mar. 2, 2015.
Notice of Reasons for Rejection for Japanese Patent Application No. 2012-557236 dated Nov. 25, 2014.
Notice of Reasons for Rejections for Japanese Patent Application No. 2011-538642, dated Oct. 1, 2013.
Patent Examination Report No. 1 for Australian Patent Application No. 2009319879 dated Nov. 10, 2014.
Patent Examination Report No. 1 for Australian Patent Application No. 2011224326 dated Apr. 21, 2015.
Second Office Action for Chinese Patent Application No. 200980155954.7, dated Oct. 24, 2013.
Second Office Action for Chinese Patent Application No. 201180013194.3, dated Mar. 23, 2015.
Smith & Nephew brochure titled "Bio RCI™ Bioabsorbable Screws: Anatomically Targeted Screws for ACL and PCL Reconstruction", 2000.
Communication from related European Application No. 14724272.1-1664 dated Jun. 13, 2017.
Second Office Action from related Chinese Application No. 201480012203.0 dated Apr. 24, 2017.
First Office Action from related Chinese Application No. 201480014353.5 dated Apr. 19, 2017.
Fourth Office Action from related Chinese Application No. 201280038677.3 dated May 26, 2017.
Second Office Action from related Chinese Application No. 201480032876.2 dated May 31, 2017.

\* cited by examiner

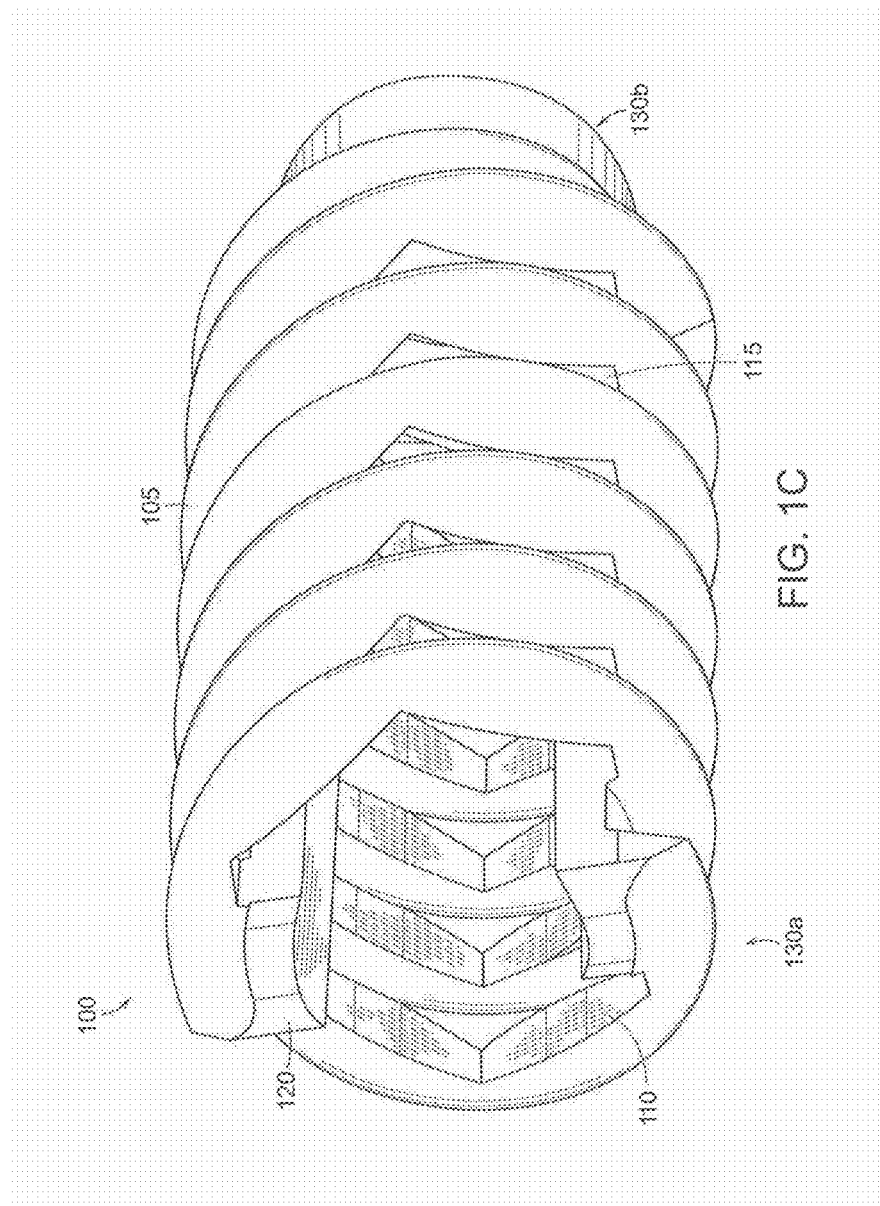

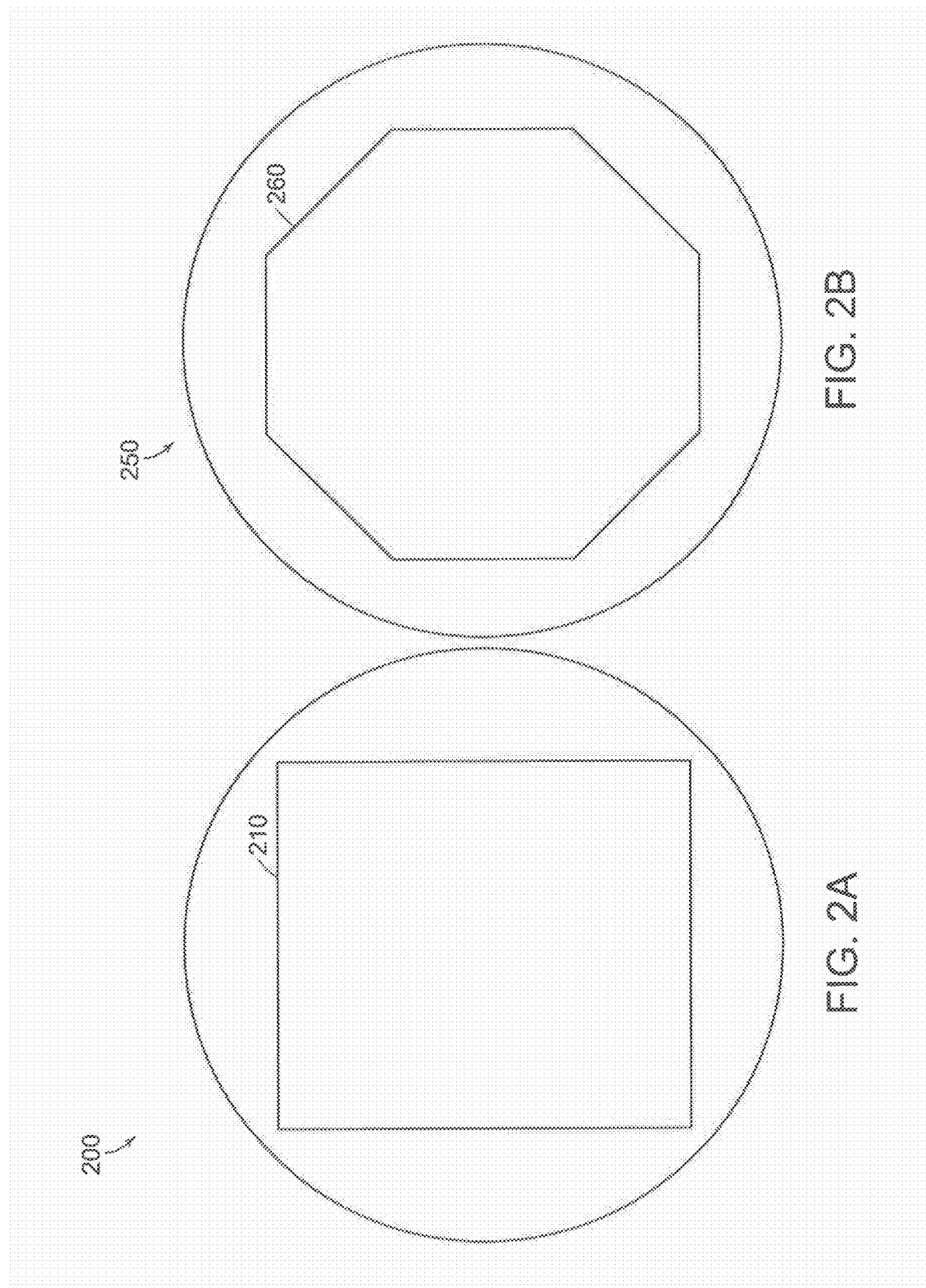

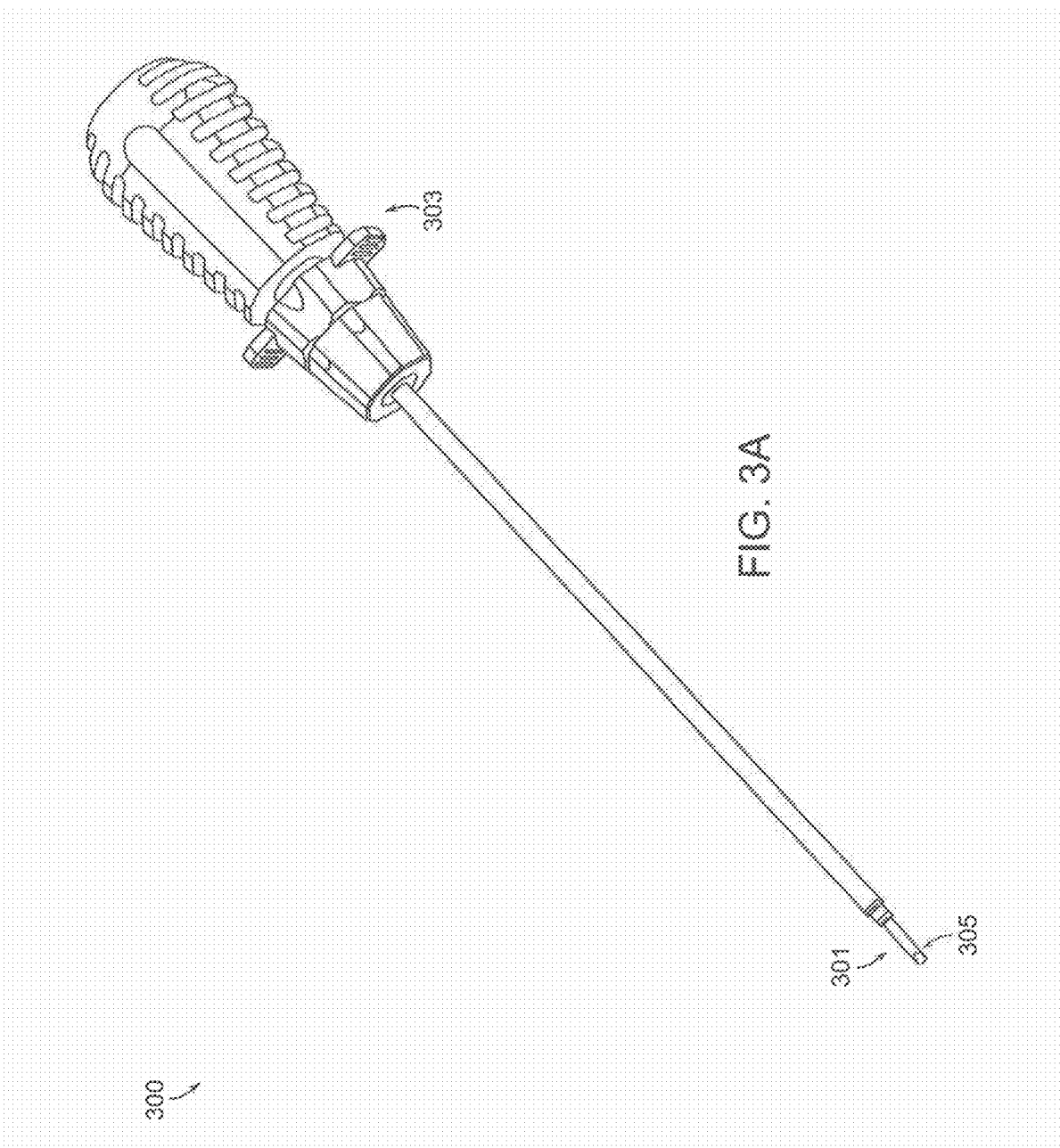

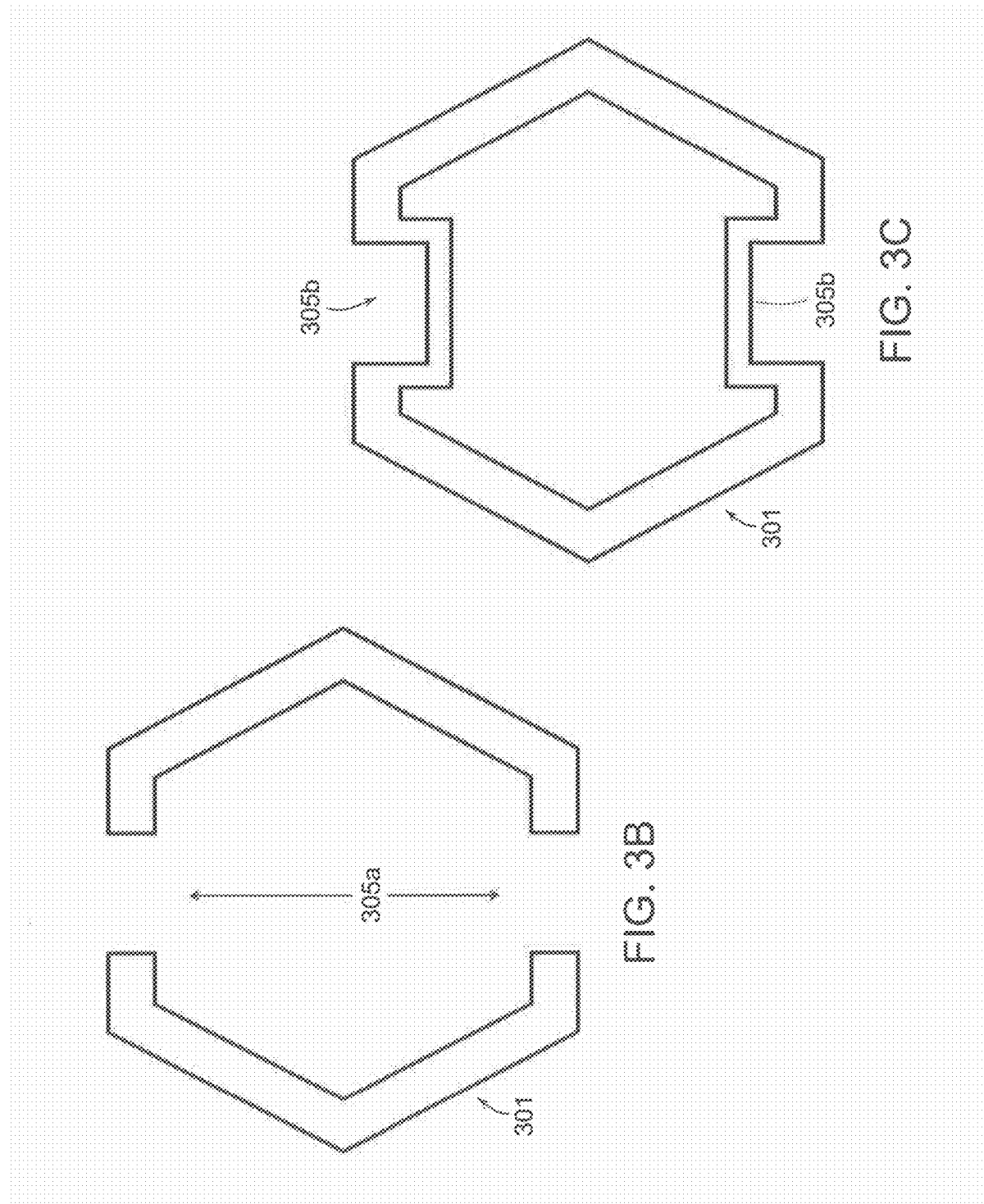

MINIATURIZED DUAL DRIVE OPEN ARCHITECTURE SUTURE ANCHOR

CROSS-REFERENCE TO RELATED APPLICATIONS

This application is a continuation application of U.S. patent application Ser. No. 13/838,942, filed Mar. 15, 2013, the disclosure of which is incorporated herein in its entirety.

BACKGROUND

Arthroscopic surgery is a minimally invasive surgical procedure in which an examination and sometimes treatment of damage of the interior of a joint is performed using an arthroscope, a type of endoscope that is inserted into the joint through a small incision. Arthroscopic procedures, such as repairing a torn rotor cuff, often require soft tissue to be reattached to bone. To achieve this, anchors (sometimes called "suture anchors") are placed in the bone and sutures attached to the anchor are passed through the tissue to securely retain the tissue in place.

SUMMARY

To reduce the amount of bone stock removed by an anchor and minimize invasiveness, ever smaller open architecture anchors are being used. However, smaller open architecture anchors result in a problematic tradeoff between reduced interior volume of the anchor and weakened drive support structure. In order to maintain structural integrity during screw-in insertion, drive elements must be capable of withstanding the torsion required for insertion of the anchor. Drive ribs are typically provided within an internal volume of an anchor to provide a structural element for a driver to apply torsion during insertion. However, as the size of the anchor is reduced, drive ribs of adequate depth/size to drive an anchor begin to occlude internal suture passages. A need therefore exists for a drive support structure to be capable of withstanding torsional drive forces during anchor insertion and to have a sufficiently small profile to avoid occlusion of internal suture passages.

The foregoing needs are addressed by an open architecture anchor having a dual drive system using both drive ribs and an internal polygonal (e.g., hexagon, octagon, square, or any other regular or irregular polygon) drive feature. This new dual drive feature allows the anchor to withstand torsional drive forces while including drive ribs of a reduced size. The internal volume of the anchor thereby is maintained such that adequate cross-sectional area is provided for the passage of sutures through the anchor and/or driver. Using a smaller anchor allows for preservation of bone stock and more rapid healing.

Accordingly, in one aspect, at least one embodiment described herein relates to an anchor for securing soft tissue to bone, for example, to repair a torn rotator cuff. The anchor includes at least one open helical coil defining a polygonal internal volume communicating with a region exterior to the at least one open helical coil through a spacing between turns of the at least one open helical coil, wherein the polygonal internal volume is sized to engage a driver. The anchor also includes at least one rib disposed within the polygonal internal volume and connected to at least two turns of the at least one open helical coil, wherein the at least one rib is sized to engage the driver and a combination of the at least one rib and the polygonal internal volume is sized to provide an anchor drive torque required to drive the anchor into bone.

Any of the embodiments described herein can include one or more of the following embodiments. In some embodiments the polygonal internal volume further comprises a cross-sectional shape including at least one of a regular polygon; irregular polygon; square, rectangle, triangle, hexagon, and/or octagon. In some embodiments, the at least one rib includes a first rib positioned on a first side of the polygonal internal volume and a second rib positioned on a second side of the polygonal internal volume. In some embodiments, the anchor also includes a suture bridge affixed to and disposed within a distal end of the anchor. In some embodiments, the at least one open helical coil is a dual lead helical coil.

In another aspect, at least one embodiment described herein provides a tissue repair system. The system includes a driver comprising a handle and a polygonal shaft connected to the handle, at least part of the polygonal shaft having a polygonal-shaped cross-section, the polygonal shaft including a distal end having at least one groove extending toward a proximal end of the polygonal shaft. The system also includes an anchor engageable with a distal end of the driver. The anchor includes at least one open helical coil defining a polygonal internal volume communicating with a region exterior to the at least one open helical coil through a spacing between turns of the at least one open helical coil, wherein the polygonal internal volume is sized to engage the polygonal shaft of the driver. The anchor also includes at least one rib disposed within the polygonal internal volume and connected to at least two turns of the at least one open helical coil, wherein the at least one rib is sized to engage the at least one groove of the driver and a combination of the at least one rib and the polygonal internal volume is sized to provide an anchor drive torque required for the driver to drive the anchor into bone.

The anchors and systems for tissue repair described herein (hereinafter "technology") can provide one or more of the following advantages. One advantage of the technology is that a smaller open architecture anchor can be provided by including a polygonal internal volume and reduced profile drive ribs. The combination of the polygonal internal volume and reduced profile drive ribs can advantageously distribute a torsional drive force, thereby maintaining structural integrity during insertion of the anchor into bone despite the reduced size and load capability of the reduced profile drive ribs. The reduced profile drive ribs advantageously allow for smaller open architecture anchors to maintain sufficiently large internal suture passages to pass one or more sutures. The open architecture of the technology advantageously allows for bony ingrowth, thereby reducing patient recovery time. The reduced size of the open architecture advantageously preserves bone stock, thereby preserving bone integrity and reducing patient recovery time. The reduced size of the open architecture also advantageously allows a higher percentage of the diameter of the anchor to be dedicated to thread depth, thereby improving fixation strength of the anchor in the bone.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The foregoing and other objects, features, and advantages will be apparent from the following more particular description of the embodiments as illustrated in the accompanying drawings in which like reference characters refer to the same parts throughout the different views. The drawings are not necessarily to scale, emphasis instead being placed upon illustrating the principles, characteristics, and features of the embodiments. In the drawings:

FIG. 1C is second isometric view of the example open architecture anchor of FIG. 1 in accordance with various embodiments.

FIGS. 2A and 2B are cross-sectional views of a polygonal internal volume of alternative open architecture anchors in accordance with various embodiments, wherein the ribs have been omitted for clarity.

FIG. 3A is an isometric view of an example anchor driver in accordance with various embodiments.

FIGS. 3B and 3C are a cross-sectional views of alternative distal ends of the example anchor driver of FIG. 3A in accordance with various embodiments.

DETAILED DESCRIPTION

The following description of examples is in no way intended to limit the disclosure, its application, or uses.

Figure 1A:
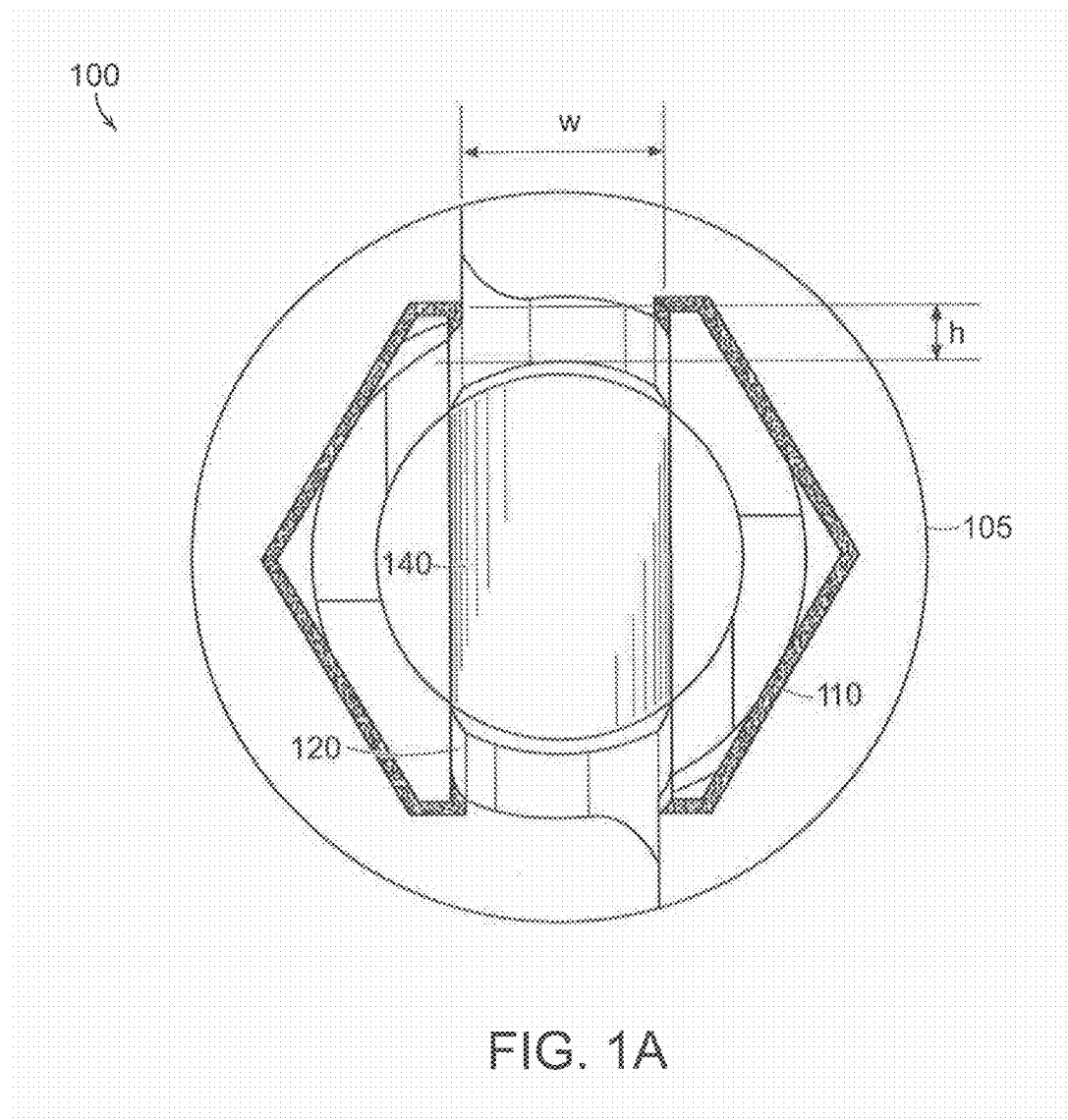
FIG. 1A is an end view of a proximal end of an example open architecture anchor in accordance with various embodiments.
Figure 1B:
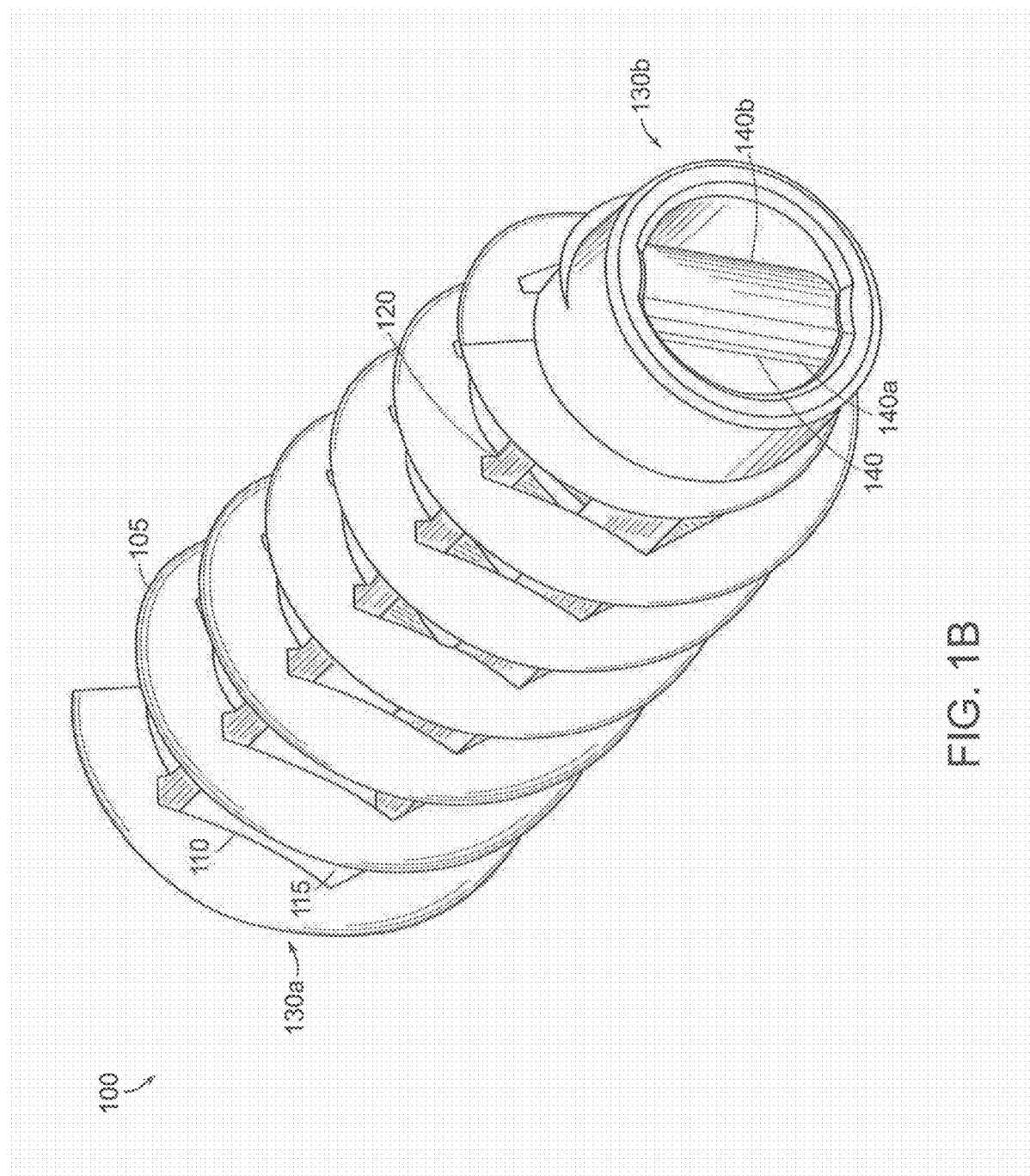
FIG. 1B is an isometric view of the example open architecture anchor of FIG. 1 in accordance with various embodiments.

FIGS. 1A-1C show an example of an anchor 100 including at least one (open) helical screw thread 105. The helical screw thread 105 defines a polygonal internal volume 110 (e.g., hexagonal as shown). The polygonal internal volume 110 communicates with a region exterior to the at least one open helical coil screw 105 through a spacing 115 between turns of the helical screw thread 105. The polygonal internal volume 110 engages a corresponding polygonal shaft of an anchor driver (e.g., polygonal shaft 301 of anchor driver 300 as shown in FIGS. 3A-3B).

In use, the anchor 100 is located at a distal end of the anchor driver such that the polygonal shaft engages the polygonal internal volume of the anchor 100. A torsional drive force is then applied to the anchor 100 by the anchor driver to insert the anchor 100 into bone. In various embodiments, the anchor driver can engage the polygonal internal volume 110 along only a portion of the longitudinal length of the anchor (i.e., from proximal end 130a to distal end 130b). Engagement of substantially the entire length of the polygonal internal volume 110 by the anchor driver, in accordance with various embodiments, can be advantageous because the torsional drive force applied to the anchor 100 during insertion can be distributed throughout the length of the anchor 100, rather than concentrated on a smaller portion of the anchor 100. After the anchor 100 is inserted into bone and the patient begins to heal, new bone grows into the internal volume 110 through the spacing 115. For faster and more complete healing, this "bony ingrowth" is highly desirable.

In another embodiment, the anchor 100 further includes at least one rib 120 (e.g., two as shown) connected to at least two turns of the helical screw thread 105. The ribs 120 engage corresponding grooves of an anchor driver (e.g., grooves 305 of anchor driver 300 as shown in FIGS. 3A-3B). In use, the anchor 100 is located at a distal end of the anchor driver such that the grooves engage the ribs 120 of the anchor 100. In various embodiments, a surgeon inserts the anchor 100 into bone using the anchor driver by applying a torsional drive force to the driver, which transmits the torsion to the anchor 100, thereby screwing the anchor into bone.

In various embodiments, engagement of the anchor driver with both the polygonal internal volume 110 and the ribs 120 of the anchor 100 advantageously distributes the torsional drive force between the ribs 120 and the polygonal internal volume 110. Such load distribution, in various embodiments, will allow the anchor 100 to withstand the torsional drive force despite having undersized drive ribs 120. For example, ribs 120 having a width (w) and/or height (h) too small to independently support the torsional drive force can be used in combination with a polygonal internal volume 110 to establish the necessary structural properties of the anchor 100. In various embodiments, the anchor driver can engage the polygonal internal volume 110 and/or the ribs 120 along only a portion of the longitudinal length of the anchor (i.e., from proximal end 130a to distal end 130b). However, engagement of substantially the entire length of the polygonal internal volume 110 and/or the ribs 120 by the anchor driver, in accordance with various embodiments, can be advantageous because the torsional drive force applied to the anchor 100 during insertion can be distributed throughout the length of the anchor 100, rather than concentrated on a smaller portion of the anchor 100. This further distribution allows further reduction in width (w) and/or height (h). The reduced width (w) and/or height (h) can, in various embodiments; advantageously prevent occlusion of a cross-sectional area of the polygonal internal volume 110 such that sutures can pass inside the anchor 100 and/or the anchor driver.

The anchor 100, in various embodiments, can also include a suture bridge 140 attached to and disposed at least partially within a distal end 130b of the anchor 100. The suture bridge 140 can be located entirely within the distal end 130b of the anchor 100 (e.g., as shown in FIG. 1B) but can also protrude distally from the distal end 130b. The suture bridge 140 can, in various embodiments, include a rounded distal-facing region around which one or more sutures can be routed. In such embodiments, a first end of each suture extends proximally through the anchor 100 on a first side of the suture bridge 140a and a second end of each suture extends proximally through the anchor 100 on a second side of the suture bridge 140b. The suture bridge 140 advantageously retains one or more sutures within the anchor 100 while preventing the cutting, pinching, and/or other weakening of the sutures associated with positioning the sutures between the anchor 100 and the bone.

Some examples of the anchor 100 include two helical screw threads 105 in a "dual lead" thread arrangement. Dual lead means that two "ridges" are wrapped around the anchor 100. The anchor 100 can be constructed from, for example but not limited to, polymers (e.g., polyetheretherketone), bioabsorbable materials, metals (e.g., surgical steel, titanium), or any other suitable material.

As shown in FIGS. 1A, 2A, and 2B, any regular polygonal or irregular polygonal shape can be used for the polygonal internal volume 110, 210, 260 of the anchor 100, 200, 250, respectively, in accordance with various embodiments. Shapes of the polygonal internal volume 110, 210, 260 can include, for example but not limited to, a hexagon (e.g., the shape of internal volume 110 as shown in FIG. 1A), a rectangle (e.g., the shape of internal volume 210 as shown in FIG. 2A), an octagon (e.g., the shape of internal volume 260 as shown in FIG. 2B), a triangle, a star-shape, a trapezoid, and/or any other suitable non-circular shape capable of engaging with a driver to receive at least a portion of a transmitted torsional drive force.

FIGS. 3A-3C show an anchor driver 300 in accordance with various embodiments. The anchor driver includes a polygonal shaft 301 connected at a proximal end to a handle 303. The polygonal shaft 301 includes one or more grooves 305 (e.g., two as shown) extending toward a proximal end of the polygonal shaft 301. The polygonal shaft 301, in various embodiments, can have a polygonal-shaped cross-section along its entire longitudinal length. In various embodiments, the polygonal shaft 301 can have a polygonal-shaped cross section along only a portion of its longitudinal length and can have at least one different cross-sectional shape (e.g., a different polygon, a circle, an ellipse) along one or more additional portions of its longitudinal length.

As shown in FIG. 3B, the one or more grooves 305 can be provided, in various embodiments, as cut-out grooves 305a which are open to an interior of the polygonal shaft 301. As shown in FIG. 3C, the one or more grooves 305 can be provided, in various embodiments, as channel grooves 305b. As described above, in various embodiments, the polygonal shaft 301 can be inserted into the polygonal internal volume (e.g., 110 as described above) of an anchor (e.g., 100 as described above) to engage the polygonal shaft 301 with the polygonal internal volume and the grooves 305 with the ribs (e.g., 120 as described above).

In various embodiments, the handle 303 can be manufactured from a polymer material and via an injection molding process. However, any other suitable material (e.g., metals, composites, wood) and/or process (e.g., extrusion, machining, electro-chemical machining) can be used. The polygonal shaft 301 and/or any surfaces defining a groove 305 thereon can be made from a metal material via an extrusion or drawing process. However, any other suitable material (e.g., plastics, composites) and/or process (e.g., injection molding, casting, machining, electro-chemical machining) can be used. The polygonal shaft 301 can be coupled to the handle 303 via an interference fit. However, any other suitable method of coupling (e.g., screws, adhesives, rivets) can be used.

Figure 4:
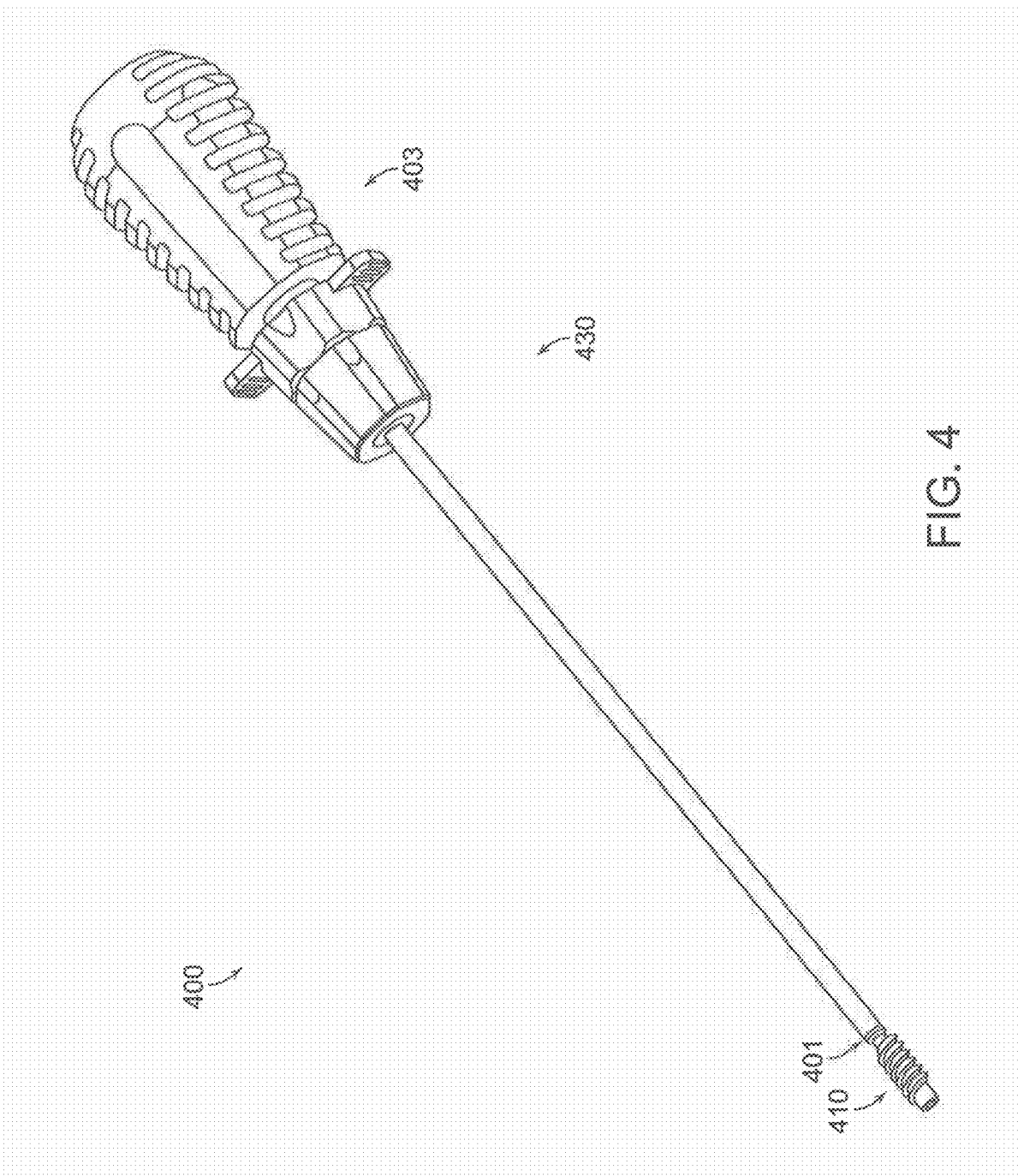
FIG. 4 is an isometric view of an example tissue fixation system in accordance with various embodiments.

FIG. 4 illustrates a tissue fixation system 400 in accordance with various embodiments. The tissue fixation system 400 includes an anchor 410 engaged with a driver 430. In various embodiments, one or more sutures (not shown) can be installed such that each suture passes around a suture bridge (e.g., 140 as shown in FIG. 1) and the ends of each suture extend toward a proximal end of the tissue fixation system 400 through the anchor 410, a grooved polygonal shaft 401 of the anchor driver 430, and/or a handle 403 of the anchor driver 430. In various embodiments, a surgeon can apply a torsional drive force to the handle 403, which transmits the torsional drive force to the grooved polygonal shaft 401 thereby applying the torsional drive force to the anchor 410 to screw the anchor 410 into bone. In various embodiments, the anchor 410 may include, for example but not limited to, any anchor 100, 200, 250 as described hereinabove with reference to FIGS. 1A-1C and FIGS. 2A-2B. In various embodiments, the anchor driver 430, the handle 403, and/or the grooved polygonal shaft 401 may include, for example but not limited to, any anchor driver 300, any polygonal shaft 301, any grooves 305, 305a, 305b, and/or any handle 303 as described hereinabove with reference to FIGS. 3A-3C.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described examples, but should be defined only in accordance with the following claims appended hereto and their equivalents.

What is claimed is:

1. An anchor comprising:
    at least one open helical coil defining a polygonal internal volume communicating with a region exterior to the at least one open helical coil through a spacing between turns of the at least one open helical coil, wherein the polygonal internal volume is sized to engage a driver; and
    at least one rib disposed within the polygonal internal volume and connected to at least two turns of the at least one open helical coil, wherein the at least one rib is sized to engage the driver and a combination of the at least one rib and the polygonal internal volume is sized to provide an anchor drive torque required to drive the anchor into bone.

2. The anchor of claim 1, wherein the polygonal internal volume further comprises a cross-sectional shape including at least one of a regular polygon, irregular polygon, ellipse, square, rectangle, hexagon, and/or octagon.

3. The anchor of claim 1, wherein the at least one rob includes a first rib positioned on a first side of the polygonal internal volume and a second rib positioned on a second side of the polygonal internal volume.

4. The anchor of claim 1, further comprising a suture bridge affixed to and disposed within a distal end of the anchor.

5. The anchor of claim 1 wherein the at least one open helical coil is a dual lead helical coil.

6. A tissue repair system comprising:
    a driver comprising a handle and a polygonal shaft connected to the handle, at least part of the polygonal shaft having a polygonal-shaped cross-section, the polygonal shaft including a distal end having at least one groove extending toward a proximal end of the polygonal shaft; and
    an anchor engageable with a distal end of the driver comprising:
        at least one open helical coil defining a polygonal internal volume communicating with a region exterior to the at least one open helical coil through a spacing between turns of the at least one open helical coil, wherein the polygonal internal volume is sized to engage the polygonal shaft of the driver, and;
        at least one rib disposed within the polygonal internal volume and connected to at least two turns of at the least one open helica coil, wherein the at least one rib is sized to engage the at least one groove of the drive and a combination of the at least one rib and one polygonal internal volume is sized to provide an anchor drive torque required for the driver to drive the anchor into bone.

* * * * *